United States Patent
Tashiro et al.

(10) Patent No.: US 7,423,266 B2
(45) Date of Patent: Sep. 9, 2008

(54) SAMPLE HEIGHT REGULATING METHOD, SAMPLE OBSERVING METHOD, SAMPLE PROCESSING METHOD AND CHARGED PARTICLE BEAM APPARATUS

(75) Inventors: Junichi Tashiro, Chiba (JP); Yutaka Ikku, Chiba (JP); Makoto Sato, Chiba (JP)

(73) Assignee: SII Nanotechnology Inc. (JP)

( * ) Notice: Subject to any disclaimer, the term of this patent is extended or adjusted under 35 U.S.C. 154(b) by 159 days.

(21) Appl. No.: 11/360,948

(22) Filed: Feb. 23, 2006

(65) Prior Publication Data
US 2006/0192118 A1    Aug. 31, 2006

(30) Foreign Application Priority Data
Feb. 25, 2005 (JP) .............................. 2005-051203

(51) Int. Cl.
*G21K 7/00* (2006.01)
*G01N 23/00* (2006.01)

(52) U.S. Cl. ................. 250/310; 250/306; 250/307; 250/309; 250/396 R; 250/491.1; 250/492.2; 250/492.21; 250/492.3

(58) Field of Classification Search ................. 250/310, 250/306, 307, 309–311, 559.29, 559.3, 548, 250/396 R, 397–400, 491.1, 492.1, 492.2, 250/492.21, 492.22, 492.3; 356/138, 139, 356/139.07, 399–401, 601, 607, 608
See application file for complete search history.

(56) References Cited

U.S. PATENT DOCUMENTS

| | | | | |
|---|---|---|---|---|
| 4,943,722 A | * | 7/1990 | Breton et al. | 250/310 |
| 5,986,264 A | * | 11/1999 | Grunewald | 250/310 |
| 6,162,735 A | * | 12/2000 | Zimmermann et al. | 438/712 |
| 6,407,398 B1 | * | 6/2002 | Kurokawa et al. | 250/492.22 |
| 6,538,249 B1 | * | 3/2003 | Takane et al. | 250/310 |
| 6,960,767 B1 | * | 11/2005 | Do et al. | 250/311 |
| 7,022,986 B2 | * | 4/2006 | Shinada et al. | 250/310 |
| 2003/0127593 A1 | * | 7/2003 | Shinada et al. | 250/310 |
| 2004/0211899 A1 | * | 10/2004 | Ezumi et al. | 250/310 |
| 2005/0061972 A1 | * | 3/2005 | Kochi et al. | 250/310 |
| 2005/0103746 A1 | * | 5/2005 | Nadeau et al. | 216/62 |
| 2006/0060781 A1 | * | 3/2006 | Watanabe et al. | 250/310 |
| 2006/0091321 A1 | * | 5/2006 | Kaga et al. | 250/491.1 |
| 2006/0126079 A1 | * | 6/2006 | Bareket et al. | 356/625 |
| 2006/0157341 A1 | * | 7/2006 | Fujii | 204/192.34 |
| 2006/0192118 A1 | * | 8/2006 | Tashiro et al. | 250/310 |
| 2006/0249676 A1 | * | 11/2006 | Shinada et al. | 250/310 |
| 2007/0109557 A1 | * | 5/2007 | Saito et al. | 356/602 |

\* cited by examiner

*Primary Examiner*—Bernard E Souw
(74) *Attorney, Agent, or Firm*—Adams & Wilks

(57) ABSTRACT

In a sample height regulating method, an area including the observation point on the sample is scan-irradiated with a first charged particle beam to obtain a first secondary electron image including the observation point. An area including the observation point on the sample is then scan-irradiated with a second charged particle beam to obtain a second secondary electron image including the observation point. Thereafter, based on magnifications of the first secondary electron image and the second secondary electron image and a distance between the observation point in the first secondary electron image and the observation point in the second secondary electron image, a height of the sample required for focusing the first charged particle beam and the second charged particle beam on the observation point is calculated. A sample stage supporting the sample is then displaced so as to position the sample at the calculated sample height.

20 Claims, 5 Drawing Sheets

SAMPLE HEIGHT REGULATING METHOD, SAMPLE OBSERVING METHOD, SAMPLE PROCESSING METHOD AND CHARGED PARTICLE BEAM APPARATUS

BACKGROUND OF THE INVENTION

The present invention relates to an apparatus for processing or observing a semiconductor wafer with a charged particle beam.

Along with advances in the level of integration and in the design rule of semiconductor devices, a micro processing/observing technology is being requested also in the defect analysis of the semiconductor devices. As a micro processing/observing technology for a defect in a semiconductor device, a cross-section observing method, for example with an FIB-SEM apparatus, of forming a cross section by an etching with an FIB and observing the cross section with an SEM is disclosed (for example cf. Patent Reference 1).

In case of a cross-sectional observation of a sample with an FIB-SEM apparatus, as the cross section formed by a focused ion beam is observed by an irradiation with an electron beam, a sample stage has to be regulated to be at such a height that the focused ion beam and the electron beam are focused on a same observation point (eucentric position) of the sample. Unless the height of the sample stage is regulated, the cross-sectional part formed by the focused ion beam may not be contained in an irradiating range of the electron beam and the sample stage may have to be displaced for observing the cross section, thereby deteriorating the efficiency of operation. Therefore, following procedure has been employed for regulating the height of the sample stage. A specified position on the sample is scan-irradiated with a charged particle beam to obtain a secondary electron image. Then the sample stage is inclined, and a scan-irradiation with a charged particle beam is executed in the inclined state to obtain a secondary electron image. A displacement amount of the specified position in thus obtained secondary electron image, from the specified position in the secondary electron image obtained prior to inclining, is determined, and the height of the sample stage is regulated so as to decrease the displacement amount (for example cf. Patent Reference 2).

However, a wafer of a diameter of 300 mm is recently introduced into the semiconductor process, and a sample of a large diameter such as a 300 mm wafer, may generate a bending in a height direction of the sample. In such case, since the sample height varies even within a same wafer, a focused ion beam and an electron beam may not be focused on a same observation point on the wafer in different positions of the wafer, even by a height regulation of the sample stage.

Patent Reference 1: JP-A-11-213935

Patent Reference 2: JP-A-2000-251823

A process of defect analysis requires an improvement in the throughput and in the precision of observation associated with a miniaturization of a part to be analyzed, and it is desired that observation and processing can be executed easily within a short time and with a high precision.

However, in the above-described method of sample height regulation based on an image displacement amount by inclining the sample, the operation efficiency is low because the sample has to be inclined. Also in case that the sample is bent in a height direction thereof as in a case of a 300 mm wafer, the operation efficiency may be lowered because the precision of observation and processing is lowered, or because the sample stage has to be displaced every time when switching between observation and processing.

The present invention is to solve such problems in the prior method and apparatus, and an object thereof is to enable observation and processing precisely and easily within a short time.

SUMMARY OF THE INVENTION

The present invention provides the following aspects for attaining the above-mentioned objects.

As a first aspect for solving the problems, a sample height regulating method of the present invention is characterized in including, in an apparatus capable of irradiating an observation point on a sample with two charged particle beams from different angles, a step of scan-irradiating an area including the observation point on the sample with a first charged particle beam to obtain a first secondary electron image including the observation point, a step of scan-irradiating an area including the observation point on the sample with a second charged particle beam to obtain a second secondary electron image including the observation point, a step of calculating, based on magnifications of the first secondary electron image and the second secondary electron image and a distance between the observation point in the first secondary electron image and the observation point in the second secondary electron image, a height of the sample required for focusing the first charged particle beam and the second charged particle beam on the observation point, and a step of displacing a sample stage so as to position the sample at the calculated sample height.

As a second aspect for solving the problems, a sample observing method of the present invention is characterized in including, a step of executing a sample height regulating method described in the first aspect at a desired observation area or in a vicinity thereof, and a step of scan-irradiating the observation area with the first charged particle beam to obtain a secondary electron image of the observation area.

Also a third aspect for solving the problems utilizes a sample height regulating method described in the first aspect, characterized in that the first charged particle beam and the second charged particle beam are respectively an electron beam and an ion beam.

As a fourth aspect for solving the problems, a sample processing method of the present invention is characterized in including a step of executing a sample height regulating method described in the third aspect, at a desired process area or in a vicinity thereof, and a step of scan-irradiating the process area with the ion beam to execute an etching on the process area.

Also a fifth aspect for solving the problems is a sample processing method characterized in including a step of executing a sample height regulating method described in the third aspect, at a desired process area or in a vicinity thereof, a step of scan-irradiating the process area with the ion beam to execute an etching on the process area, and a step of scan-irradiating a cross section, prepared by the etching, with the electron beam to observe the cross section.

As a sixth aspect for solving the problems, a charged particle beam apparatus of the present invention is characterized in including a first charged particle source for generating first charged particles, a first charged particle optical system for focusing the first charged particles into a first charged particle beam and irradiating a sample surface with the first charged particle beam under a scanning motion, a second charged particle source for generating second charged particles, a second charged particle optical system for focusing the second charged particles into a second charged particle beam and irradiating the sample surface with the second charged particle beam under a scanning motion, a secondary electron detector for detecting secondary electrons generated by irradiating the sample surface with the first charged particle beam or the second charged particle beam, display means which displays a secondary electron image based on the secondary electrons detected by the secondary electron detector, calculation means which calculates a height of the sample at which the first charged particle beam and the second charged particle beam are focused on an observation point on the sample, a sample stage for supporting the sample, and displacement means which displaces the sample stage to the height calculated by the calculation means.

As a seventh aspect for solving the problems, a charged particle beam apparatus described in the sixth aspect is characterized in that the calculation means calculates the height of the sample at which the first charged particle beam and the second charged particle beam are focused on the observation point on the sample, from a first secondary electron image obtained by scan-irradiating the observation point on the sample with the first charged particle beam and a second secondary electron image obtained by scan-irradiating the observation point on the sample with the second charged particle beam, based on magnifications of the first secondary electron image and the second secondary electron image and on a distance between the observation point in the first secondary electron image and the observation point in the second secondary electron image.

As an eighth aspect for solving the problems, a charged particle beam apparatus described in the sixth aspect is characterized in that the first charged particle beam and the second charged particle beam are respectively an electron beam and an ion beam.

The first aspect has a following effect. By the step of calculating, based on magnifications of the first secondary electron image and the second secondary electron image and a distance between the observation point in the first secondary electron image and the observation point in the second secondary electron image, a height of the sample required for focusing the first charged particle beam and the second charged particle beam on the observation point, and by displacing a sample stage so as to position the sample at the calculated sample height, the sample can be positioned so that the observation point can be irradiated with the two charged particle beams.

The fourth aspect has a following effect. By executing a sample height regulating method described in the third aspect, at a desired process area or in a vicinity thereof, and by executing an etching on the process area, the etching of such process area can be executed at a sample height at which the observation point of the sample can be irradiated with the two charged particle beams.

The fifth aspect has a following effect. By the step of executing a sample height regulating method described in the third aspect, at a desired process area or in a vicinity thereof, the step of scan-irradiating the process area with the ion beam to execute an etching on the process area, and the step of scan-irradiating a cross section, prepared by the etching, with the electron beam to observe the cross section, the cross-sectional part processed by the ion beam can be observed within an irradiation range of the electron beam.

The sixth aspect has a following effect. By employing the calculation means which calculates a height of the sample at which the first charged particle beam and the second charged particle beam are focused on an observation point on the sample, a position at which the observation point on the sample can be irradiated with the two charged particle beams can be calculated.

A sample height regulation can be easily and precisely achieved within a short time without inclining a sample stage, by calculating a sample height at which two charged particle can be focused on a same observation point, based on magnifications of two secondary electron images obtained by irradiations of two charged particle beams from different angles and on a distance between the observation points in the two secondary electron images.

Also an observation or a processing can be executed easily and precisely even in case that the sample involves a bending in the direction of height thereof, by executing the sample height regulation at an observation or processing area, or in the vicinity thereof.

Also, since the sample height regulation, observation and processing can be executed precisely and easily, an observation or a processing can be executed precisely and automatically, even in case of executing an observation or a processing on plural positions in a sample involving a bend in the height direction thereof, by programming the above-described process of sample height regulation, observation and processing in the charged particle beam apparatus.

BRIEF DESCRIPTION OF THE DRAWINGS

FIG. 2A shows a wafer and FIG. 2B shows a die.

FIGS. 4A-4B are schematic views showing positional relationship among a wafer, an ion beam and an electron beam; and FIGS. 4C-4F are secondary electron images of a die reference point.

Figure 1:
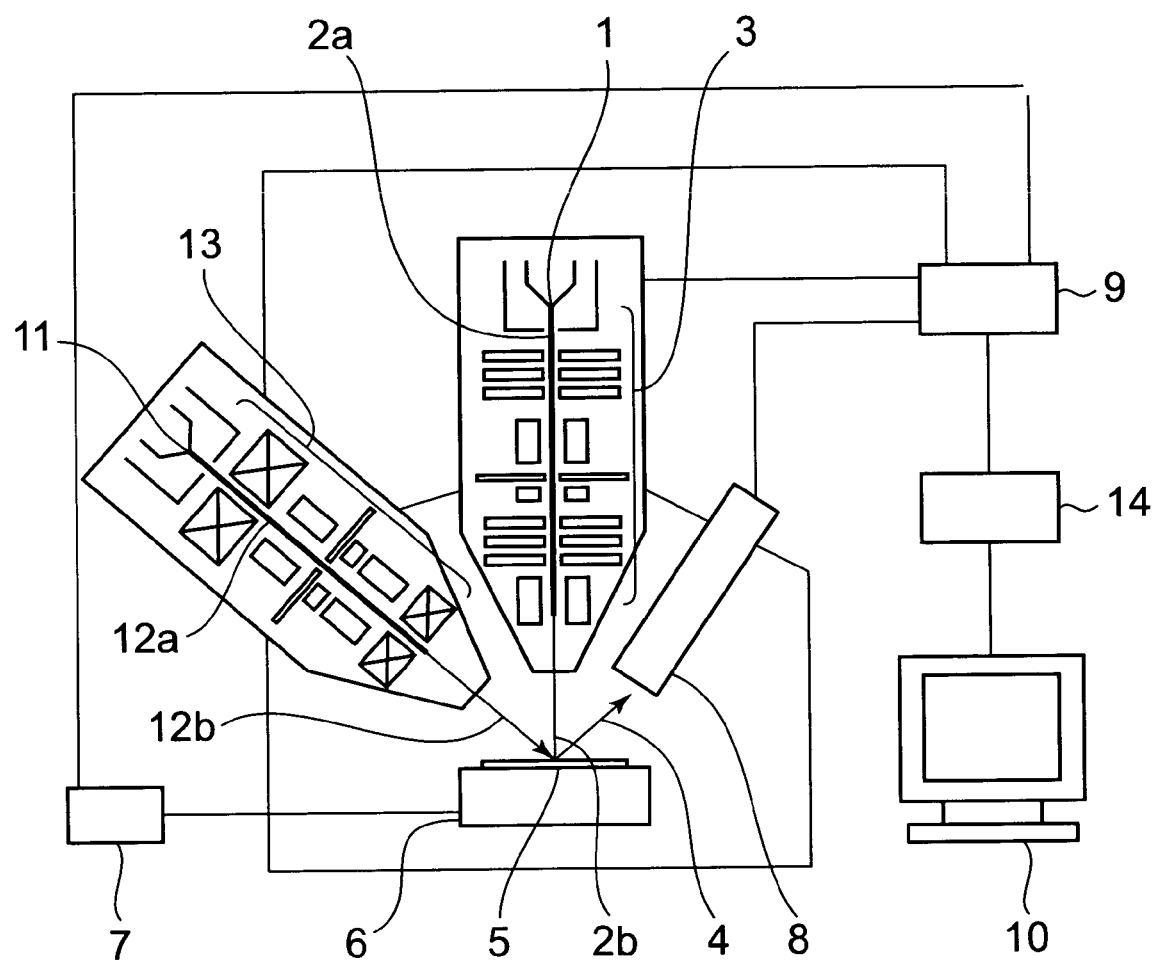
FIG. 1 is a schematic view of a charged particle beam apparatus in an embodiment of the present invention.

DESCRIPTION OF THE REFERENCE NUMERALS AND SIGNS 1 ion source
2a ions
2b ion beam
3 ion optical system
4 secondary electrons
5 wafer
5a processed groove
5b processed groove
6 sample stage
7 sample stage control means
8 secondary electron detector
9 control means
10 display means
11 electron source
12a electrons
12b electron beam
13 electron optical system
14 calculation means
15a reference point
15b reference point
15c reference point
15d reference point
16a die
16b die 16c die
16d die
17a die reference point
17b die reference point
17c die reference point
17d die reference point
18a process area
18b process area
19 calculated die reference point.

DETAILED DESCRIPTION OF THE INVENTION

In the following, embodiments of the present invention will be explained with reference to FIGS. 1, 2A-2B, 3, 4A-4F and 5A-5B.

FIG. 1 is a schematic view of a charged particle beam apparatus constituting an embodiment of the invention. Ions 2a generated by a ion source 1 are focused by an ion optical system 3 into an ion beam 2b, which is scan-irradiated on a wafer 5 constituting a sample. Also electrons 12a generated by an electron source 11 are focused by an electron optical system 13 into an electron beam 12b, which is scan-irradiated on the wafer 5. The wafer 5 is supported on a sample stage 6 which can be displaced by sample stage control means 7. Secondary electrons 4, generated by the irradiation of the wafer 5 with the ion beam 2b or the electron beam 12b, are detected by a secondary electron detector 8. The detected secondary electrons 4 are converted into luminance signals, thereby displaying a secondary electron image on a display 10. Calculation means 14 calculates a height regulation value for the wafer 5, based on a secondary electron image obtained by the irradiation with the ion beam 2b and a secondary electron image obtained by the irradiation with the electron beam 12b. The changed particle beam apparatus includes control means 9 for controlling operation of the ion source 1, electron source 11, sample stage control means 7, and calculation means 14, for example.

Figure 2A:
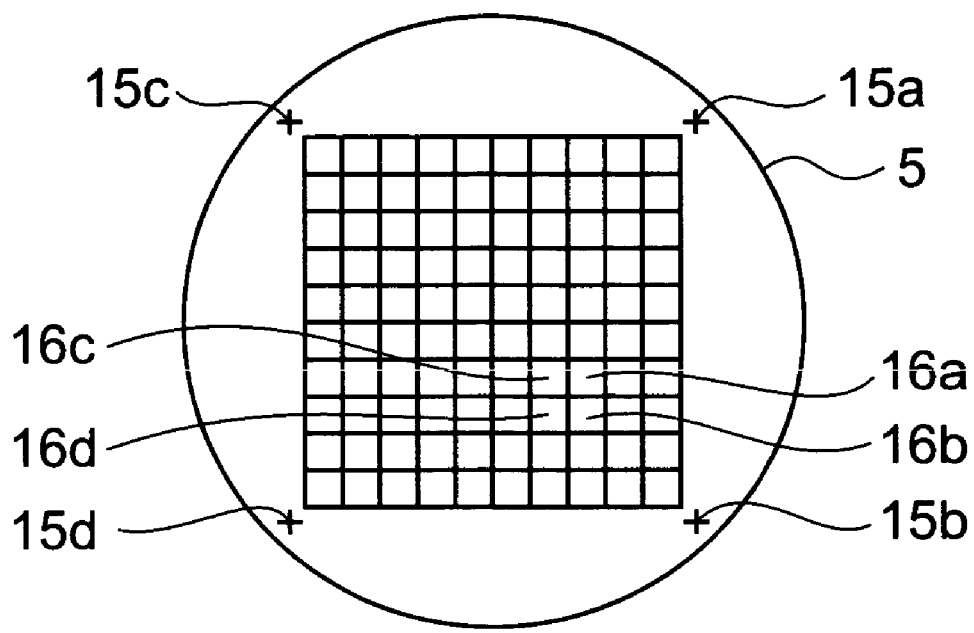
FIGS. 2A-2B are schematic views showing a sample in an embodiment of the present invention.
Figure 2B:
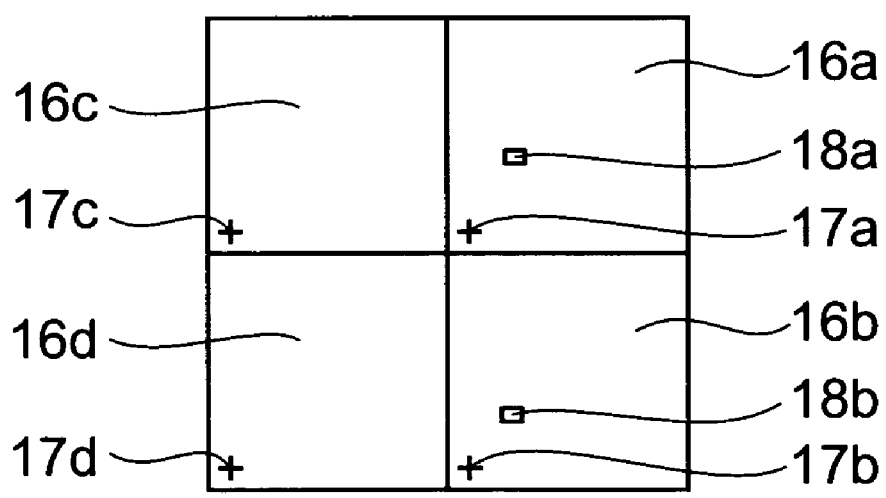

FIGS. 2A-2B are schematic views of a sample, showing an embodiment of the invention, wherein FIG. 2A is a schematic view of a wafer and FIG. 2B is a schematic view of a die in the wafer. A die is a unit in an assembly of devices present in a wafer. The wafer 5 is of a diameter of 300 mm, and dies 16a, 16b, 16c and 16d include die reference points 17a, 17b, 17c and 17d and desired positions 18a and 18b to be processed.

Figure 3:
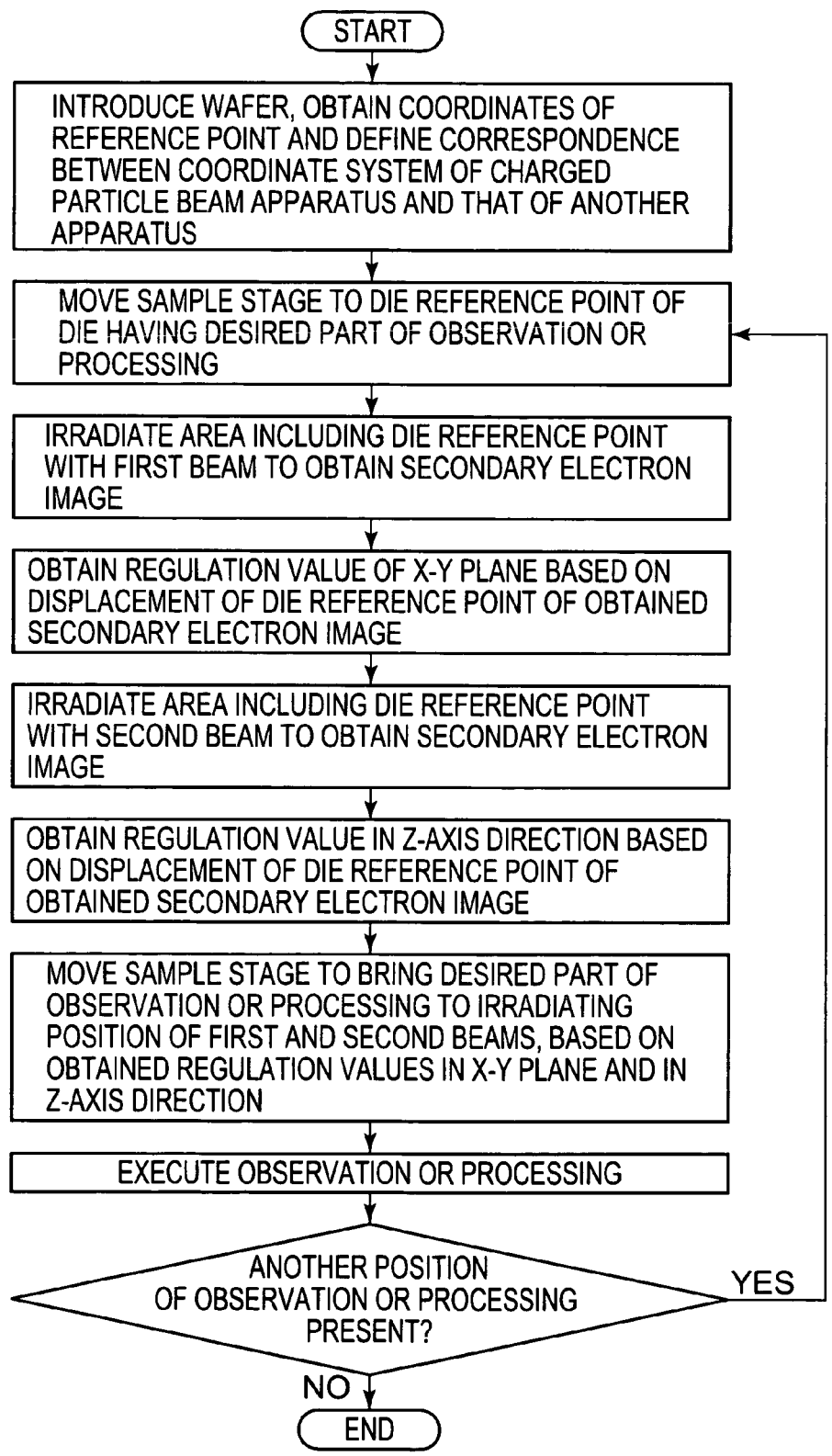
FIG. 3 is a flow chart showing a processing method of the present invention.

FIG. 3 is a flow chart showing a sample processing method of the invention, and a method for processing a wafer containing a desired process area will be explained with reference to the flow chart.

Coordinate values of the reference points 15a, 15b, 15c, 15d of the wafer 5 and those of the desired process areas 18a, 18b shown in FIG. 2, detected in advance in another apparatus, are entered into the charged particle beam apparatus. The reference point means a mark provided on the wafer. Heights of the ion optical system 3, the electron optical 13 and the sample stage 6 are regulated in advance, utilizing the ion beam 2b and the electron beam 12b respectively as a first beam and a second beam, in such a manner that the ion beam 2b and the electron beam 12b are focused on a same point on the wafer.

At first, the wafer 5 is introduced into the charged particle beam apparatus. Then, based on the coordinates of the reference point 15a, entered in advance to the charged particle beam apparatus, the sample stage 6 is displaced to a position where the reference point 15a can be irradiated with the ion beam 2b. Then an area including the reference point 15a is scan-irradiated by the ion beam 2b to obtain a secondary electron image. Coordinates of the reference point 15a are stored from the obtained secondary electron image. This step is conducted also on the reference points 15b, 15c and 15d. Thus, conversion coefficients are determined for converting the coordinate system of another apparatus into the coordinate system of the sample processing apparatus, thereby defining a correspondence between the coordinate systems of the apparatuses. Then the conversion coefficients determined in the above-explained step are used to calculate the coordinates of the desired process areas 18a, 18b in the coordinate system of the charged particle beam apparatus, from those of the process areas stored in the coordinate system of another apparatus. Also coordinates of the die reference points 17a, 17b, 17c and 17d are calculated in a similar manner. A die reference point means a mark provided in each die present on the wafer.

Then a secondary electron image is obtained of the die reference point 17a of a die 16a containing a process area 18a, for recognizing a more accurate position of the die reference point 17a. At first, the sample stage 6 is displaced to a position where the die reference point 17a can be irradiated with the ion beam 2b. Then the ion beam 2b is scan-irradiated on the surface of the wafer 5 to obtain a secondary electron image. A regulation value in an X-Y plane is calculated and stored, from a displacement amount between a position of the die reference point 17a in the obtained secondary electron image, and the calculated position of the die reference point 17a. Then the surface of the wafer 5 is scan-irradiated with the electron beam 12b to obtain a secondary electron image. A position of the die reference point 17a in the secondary electron image obtained by the irradiation with the electron beam 12b is compared with a position of the die reference point 17a in the secondary electron image obtained by the irradiation with the ion beam 2b, and a regulation value in a Z-axis direction is calculated and memorized by the calculation means 14, from the displacement amount in the comparison. In this manner it is possible to recognize the position of the die reference point 17a positioned close to the process area 18a, and to calculate a correction value therefor. A method for calculating the regulation value from the obtained secondary electron images will be explained with reference to FIG. 4.

Figure 4A:
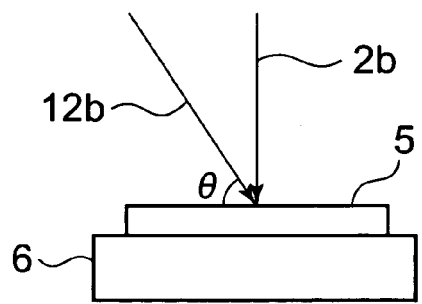
FIGS. 4A-4F are views for explaining the height position regulating method of the present invention.
Figure 4B:
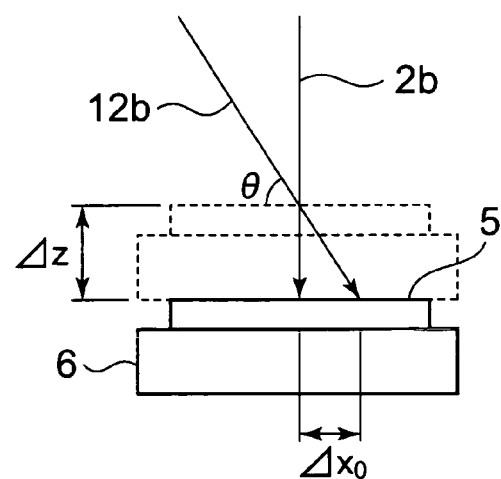
Figure 4C:
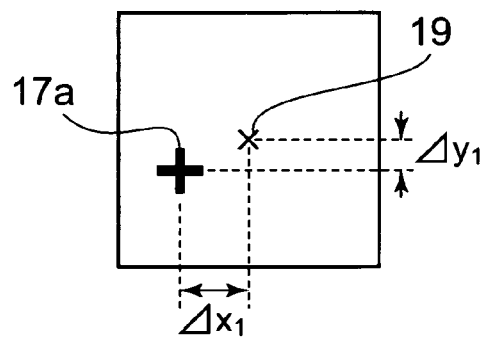

FIGS. 4A-4F are views for explaining the height position regulating method of the invention. FIGS. 4A and 4B are schematic views showing a positional relationship among the wafer, the ion beam and the electron beam, and FIGS. 4C-4F are secondary electron images of an area including the die reference point 17a. FIG. 4A is a schematic view showing a state in which the wafer 5 is positioned at a height where the ion beam 2b and the electron beam 12b are focused on a same point on the wafer 5. The wafer 5 having a horizontal surface is placed on a sample stage having a horizontal surface. The ion beam 2b enters in a direction perpendicular to the wafer surface. The electron beam 12b enters with an angle θ inclined from the horizontal plane. FIG. 4C shows a secondary electron image of the area including the die reference point 17a, obtained by the irradiation with the ion beam 2b in such state. A point 19 indicates a position of the die reference point 17a calculated in the above-described position recognizing step by the reference points, and is displaced from the die reference point 17a in the secondary electron image by $\Delta X_1$ and $\Delta Y_1$ respectively in X- and Y-axis directions. Values required for correcting such displacement can be calculated and stored as regulation values for the X-Y plane.

Figure 4D:
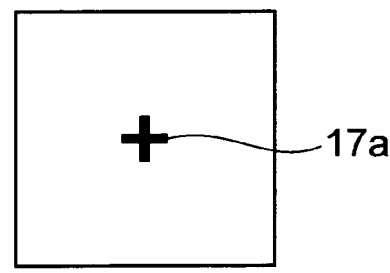
Figure 4E:
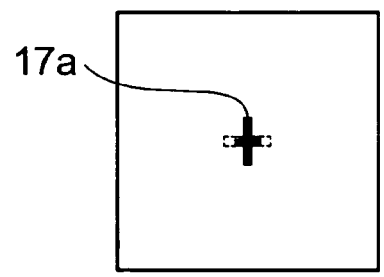

Then, FIG. 4D shows a secondary electron image obtained by the irradiation with the ion beam 2b, with the die reference point 17a at the center. FIG. 4E shows a secondary electron image obtained in this state by the irradiation with the electron beam 12b. Since the electron beam 12b enters the water 5 with an angle θ, the secondary electron image is obtained as an image observing the wafer 5 from an inclined direction. A broken-lined image indicates the position of the die reference point 17a in the secondary electron image shown in FIG. 4D. When the wafer is positioned at a height, at which the ion beam 2b and the electron beam 12b are focused on a same observation point on the wafer 5, the central position of the secondary electron image formed by the irradiation with the ion beam 2b and that of the secondary electron images formed by the irradiation with the electron beam 12b correspond.

Figure 4F:
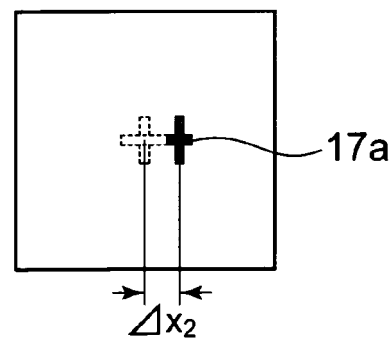

On the other hand, FIG. 4B is a schematic view showing a state in which the wafer 5 is in a position lower by ΔZ than the position where the ion beam 2b and the electron beam 12b are focused in a same observation point on the wafer 5. Broken lines indicate the wafer 5 and the sample stage 6 at a height of wafer 5 at which the ion beam 2b and the electron beam 12b are focused in a same observation point. $\Delta X_0$ indicates a displacement amount between a position where the ion beam 2b is focused on the wafer 5 and a position where the electron beam 12b is focused on the wafer 5. FIG. 4F shows a secondary electron image obtained in such state by the irradiation with the electron beam 12b. A broken-lined image indicates the position of the die reference point 17a in the secondary electron image obtained by the irradiation with the ion beam 2b, and displayed in a position with a distance of $\Delta X_2$ from the position of the die reference point in the secondary electron image obtained by the irradiation with the electron beam 12b. Since the wafer 5 is positioned lower, by ΔZ, than the broken-lined height of the wafer 5 at which the ion beam 2b and the electron beam 12b are focused on a same observation point, the electron beam 12b is focused at a position with a distance of $\Delta X_0$ from the focusing point of the ion beam 2b. Therefore, in the secondary electron image obtained by the irradiation with the electron beam 12b, the die reference point 17a is displayed in a position with a distance of $\Delta X_2$ from the center of the image.

Here, $\Delta X_0$, $\Delta X_2$ and $\Delta Z$ are correlated by the following relations:

$$\Delta Z = \Delta X_0 \cdot \tan \theta$$

$$\Delta X_2 = k \cdot \Delta X_0 \cdot \sin \theta$$

wherein k is a display magnification of the secondary electron image shown in FIG. 4F.

Thus, $\Delta X_2$ can be represented by:

$$\Delta X_2 = k \cdot \Delta Z \cdot \cos \theta.$$

Therefore, a displacement amount ΔZ from the height at which the ion beam 2b and the electron beam 12b are focused in a same observation point on the wafer 5 can be obtained by calculating $\Delta X_2$ from the secondary electron image formed by the irradiation with the electron beam 12b as shown in FIG. 4F. A value for correcting such displacement can be calculated and stored as a regulation value in the Z-axis direction.

Then the regulation values $\Delta X_1$ and $\Delta Y_1$ in the X-Y plane and the regulation value ΔZ in the Z-axis direction, calculated in the position recognizing step based on the die reference points, are applied to the coordinate values of the process area 18a, calculated in the position recognizing step based on the reference points, to calculate an exact position of the process area 18a, and the sample stage 6 is moved so that the calculated position can be irradiated with the ion beam 2b. Then the process area 18a is scan-irradiated with the ion beam 2b to execute an etching, and with the electron beam 12b to execute a cross-sectional observation.

Now the method of sample processing and cross-sectional observation after the above-described position regulation will be explained with reference to FIG. 5.

Figure 5A:
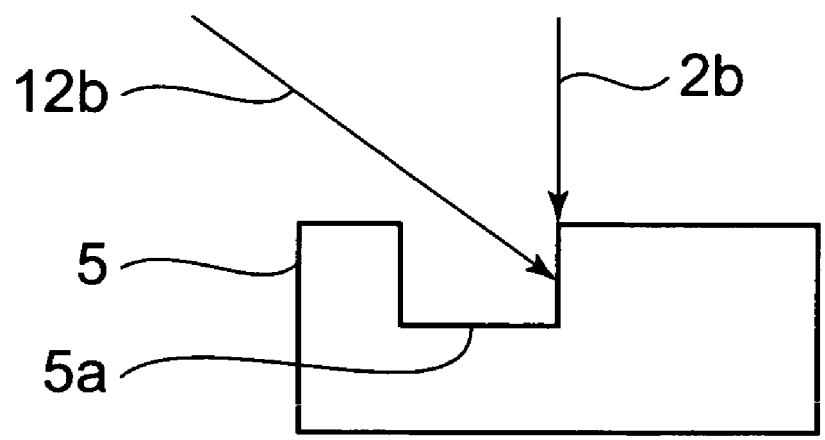
FIGS. 5A-5B are schematic views of a sample, for explaining a sample processing and cross-sectional observation method of the present invention.
Figure 5B:
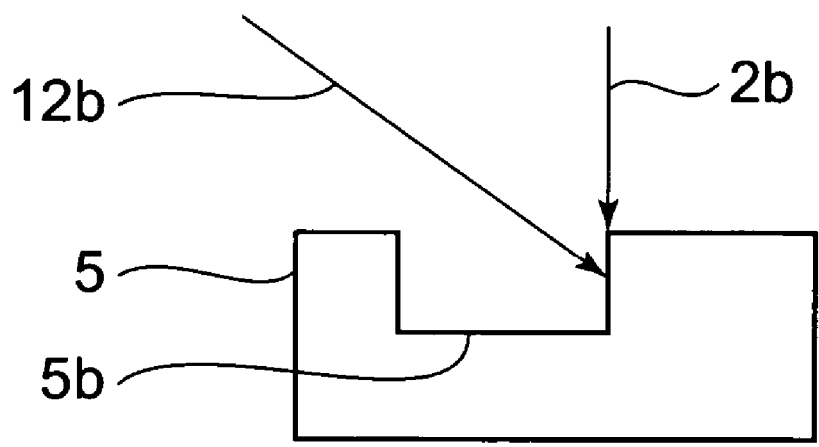

FIGS. 5A-5B show schematic views for explaining the sample processing method and the cross-sectional observation method of the invention. At first the surface of the wafer 5 is scan-irradiated with the ion beam 2b to execute an etching, thereby forming a processed groove 5a as shown in FIG. 5A. Then a cross-sectional part of the processed groove 5a is irradiated with the electron beam 12b to obtain a secondary electron image of the cross section. Then a part next to the processed groove 5a is scan-irradiated with the ion beam 2b so as to widen the processed groove 5a, whereby a processed groove 5b as shown in FIG. 5B can be obtained. Then a cross-sectional part of the processed groove 5b is irradiated with the electron beam 12b to obtain a secondary electron image of the cross section. By repeating such step, images of cross sections prepared by the etching can be obtained in succession, it is possible to confirm the processing position and, by adding the secondary electron images, to obtain a three-dimensional secondary electron image of the processed part.

When the processing is completed, and in case another part to be processed is present, the sample stage 6 is moved to a position where the die reference point including such process area can be irradiated with the ion beam 2b and the above-described step is repeated.

As explained in the foregoing, by calculating the correction values for the X-Y plane and for the Z-axis with a die reference point closed to the area to be processed and recognizing the position of the processing position by these correction values, it is rendered possible to exactly irradiate the processing position with the ion beam for processing and to exactly irradiate the processed cross section with the electron beam. Also the above described process may be programmed in the charged particle beam apparatus to realize an automated process, thereby achieving a processing and obtaining an image of the processed cross section in easy and exact manner.

What is claimed is:

1. A sample height regulating method for irradiating an observation point on a sample with two charged particle beams from different angles, comprising the steps of:

scan-irradiating an area including the observation point on the sample with a first charged particle beam to obtain a first secondary electron image including the observation point;

scan-irradiating an area including the observation point on the sample with a second charged particle beam to obtain a second secondary electron image including the observation point;

calculating, based on magnifications of the first secondary electron image and the second secondary electron image and a distance between the observation point in the first secondary electron image and the observation point in the second secondary electron image, a height of the sample required for focusing the first charged particle beam and the second charged particle beam on the observation point; and displacing a sample stage so as to position the sample at the calculated sample height.

2. A sample observing method comprising the steps of:

executing a sample height regulating method according to claim 1 at a desired observation area or in a vicinity thereof; and scan-irradiating the observation area or the vicinity thereof with the first charged particle beam to obtain a secondary electron image of the observation area.

3. A sample height regulating method according to claim 1; wherein the first charged particle beam is an electron beam and the second charged particle beam is an ion beam.

4. A sample processing method comprising the steps of:
executing a sample height regulating method according to claim 3 at a desired process area or in a vicinity thereof; and
scan-irradiating the process area or the vicinity thereof with the ion beam to etch the process area.

5. A sample processing method comprising the steps of:
executing a sample height regulating method according to claim 3 at a desired process area or in a vicinity thereof;
scan-irradiating the process area or the vicinity thereof with the ion beam to etch the process area; and
scan-irradiating a cross-section of the etched process area or vicinity thereof with the electron beam to observe the cross section.

6. A charged particle beam apparatus comprising:
a first charged particle source for generating first charged particles;
a first charged particle optical system for focusing the first charged particles into a first charged particle beam and irradiating an area including an observation point on a surface of a sample with the first charged particle beam under a scanning motion;
a second charged particle source for generating second charged particles;
a second charged particle optical system for focusing the second charged particles into a second charged particle beam and irradiating the area including the observation point on the surface of the sample with the second charged particle beam under a scanning motion;
a secondary electron detector that detects secondary electrons generated by irradiating the sample surface with the first charged particle beam or the second charged particle beam;
display means for displaying a secondary electron image based on the secondary electrons detected by the secondary electron detector;
calculation means for calculating a height of the sample required for focusing the first charged particle beam and the second charged particle beam on the observation point on the surface of the sample;
a sample stage for supporting the sample; and
displacement means for displacing the sample stage to position the sample at the height calculated by the calculation means.

7. A charged particle beam apparatus according to claim 6; wherein the calculation means calculates the height of the sample based on magnification of a first secondary electron image obtained by scan-irradiating the observation point on the surface of the sample with the first charged particle beam, magnification of a second secondary electron image obtained by scan-irradiating the observation point on the surface of the sample with the second charged particle beam, and a distance between the observation point in the first secondary electron image and the observation point in the second secondary electron image.

8. A charged particle beam apparatus according to claim 6; wherein the first charged particle beam is an electron beam and the second charged particle beam is an ion beam.

9. A sample height regulating method according to claim 1; wherein the step of scan-irradiating with the first charged particle beam comprises scan-irradiating with the first charged particle beam using a first charged particle source; and wherein the step of scan-irradiating with the second charged particle beam comprises scan-irradiating with the second charged particle beam using a second charged particle source different from the first charged particle source.

10. A sample height regulating method according to claim 9; wherein the first charged particle source is a scanning electron microscope and the second charged particle source is a focused ion beam apparatus.

11. A charged particle beam apparatus according to claim 6; wherein the first charged particle source is a scanning electron microscope and the second charged particle source is a focused ion beam apparatus.

12. A charged particle beam apparatus according to claim 11; wherein the first charged particle beam is an electron beam and the second charged particle beam is an ion beam.

13. A charged particle beam apparatus according to claim 7; wherein the first charged particle beam is an electron beam and the second charged particle beam is an ion beam.

14. A charged particle beam apparatus comprising:
a first charged particle source that generates first charged particles and focuses them into a first charged particle beam that is irradiated on an area including an observation point on a surface of a sample using a scanning motion of the first charged particle beam;
a second charged particle source that generates second charged particles and focuses them into a second charged particle beam that is irradiated on the area of the sample surface including the observation point using a scanning motion of the second charged particle beam;
a secondary electron detector that detects secondary electrons generated when the sample surface is irradiated with the first charged particle beam or the second charged particle beam;
a display that displays a secondary electron image in accordance with the secondary electrons detected by the secondary electron detector;
a calculating device that calculates a height of the sample required for focusing the first charged particle beam and the second charged particle beam on the observation point on the sample surface; and
a displacement device that displaces the sample to position the sample at the height calculated by the calculating device.

15. A charged particle beam apparatus according to claim 14; wherein the first charged particle beam is an electron beam and the second charged particle beam is an ion beam.

16. A charged particle beam apparatus according to claim 14; wherein the first charged particle source is a scanning electron microscope and the second charged particle source is a focused ion beam apparatus.

17. A charged particle beam apparatus according to claim 16; wherein the first charged particle beam is an electron beam and the second charged particle beam is an ion beam.

18. A charged particle beam apparatus according to claim 14; wherein the calculation device calculates the height of the sample based on magnification of a first secondary electron image obtained by scan-irradiating the observation point on the surface of the sample with the first charged particle beam, magnification of a second secondary electron image obtained by scan-irradiating the observation point on the surface of the sample with the second charged particle beam, and a distance between the observation point in the magnified first secondary electron image and the observation point in the magnified second secondary electron image.

19. A charged particle beam apparatus according to claim 14; further comprising a sample stage that supports the sample; and wherein the displacement device displaces the sample stage to position sample at the height of the sample calculated by the calculating device.

20. A sample height regulating method comprising:
focusing first charged particles into a first charged particle beam and irradiating the first charged particle beam on an area including an observation point on a surface of a sample using a scanning motion of the first charged particle beam;
focusing second charged particles different from the first charged particles into a second charged particle beam and irradiating the second charged particle beam on the area of the sample surface including the observation point using a scanning motion of the second charged particle beam;
detecting secondary electrons generated when the sample surface is irradiated with the first charged particle beam or the second charged particle beam;
calculating a height of the sample required for focusing the first charged particle beam and the second charged particle beam on the observation point on the sample surface; and
positioning the sample at the calculated height.

* * * * *